US00PP09488P

United States Patent [19]

Endisch et al.

[11] Patent Number: Plant 9,488

[45] Date of Patent: Mar. 26, 1996

[54] GERANIUM PLANT NAMED LORCA

[75] Inventors: Gerd Endisch, Geranienweg, D-76767, Hagenbach; Ursula Endisch-Burmeister, Bad Kreuznach, both of Germany; Wolf Endisch, Teneriffa, Spain

[73] Assignee: Gerd Endisch, Hagenbach, Germany

[21] Appl. No.: 384,008

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 6,247 8/1988 Craig ..... Plt./87.12

P.P. 8,712 5/1994 Schumann ..... Plt./87.12

P.P. 9,110 4/1995 Klemm ..... Plt./87.12

*Primary Examiner*—James R. Feyrer

*Attorney, Agent, or Firm*—Willian Brinks Hoper Gilson & Lione

[57] ABSTRACT

A new and distinct cultivar of geranium known by the cultivar name 'Lorca' is characterized by a pink with red/purple flower color, a semi-double flower form, medium green foliage, medium height, large umbels and early flower response.

1 Drawing Sheet

BACKGROUND OF THE NEW PLANT

The present invention comprises a new and distinct cultivar of geranium botanically known as *Pelargonium zonale*, and hereinafter referred to by the cultivar name 'Lorca'.

'Lorca' is a product of planned breeding program which had the objective of creating new geranium cultivars with pink flower color, dark eye, semi-double flower form and early flower response. 'Lorca' was originated from a hybridization made in a controlled breeding program in Hagenbach, Germany, in 1990.

The female parent was 'PAC Laura', characterized by its pink flower color, semi-double flower form and light green foliage without zonation. 'PAC Laura' is commercially available from PAC Dresben, Germany. The male parent of 'Lorca' was 'Rio', characterized by its pink flower colors, single flower form, dark foliage and weak habit, which is commercially available. 'Lorca' differs from 'PAC Laura' by its larger umbels and its higher and darker leaves. 'Lorca' also has a red-purple spot on broad petals where as 'PAC Laura' has a white zone at the base of its petal. 'Lorca' may be distinguished from 'Rio' by its semi-double flower and darker leaves.

'Lorca' was discovered and selected as one flowering plant within the progeny of the stated cross by the inventors in August 1991 in a controlled Environment in Hagenbach, Germany.

DESCRIPTION OF THE NEW PLANT

The first act of asexual reproduction of 'Lorca' was accomplished when vegetative cuttings were taken from the initial selection in January 1992 in a controlled environment in Hagenbach, Germany, by a technician working under formulations established and supervised by Gerd Endisch.

Horticultural examination of selected units initiated in May 1992 has demonstrated that the combination of characteristics as herein disclosed for 'Lorca' are firmly fixed and are retained through successive generations of asexual reproduction.

'Lorca' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. The dimensions and measurements given below are approximate.

The following traits have been repeatedly observed and are determined to be basic characteristics of 'Lorca' to distinguish this geranium as a new and distinct cultivar:

1. pink (with red/purple) flower color
2. semi-double flower form
3. medium green foliage
4. medium height
5. large umbels
6. early flower response.

Of the many commercial cultivars known to the present inventor, the most similar in comparison to 'Lorca' is 'Ganymed'. Reference is made to Chart A below which compares certain characteristics of 'Lorca' to those same characteristics of 'Ganymed'. In comparison to 'Ganymed', 'Lorca' has a larger umbel, longer peduncle length, smaller corolla and white zone at the base of upper petal.

BRIEF DESCRIPTION OF THE DRAWING

The accompanying photographic drawing show typical flower and foliage characteristics of 'Lorca', with colors being as true as possible with illustrations of this type.

DETAILED BOTANICAL DESCRIPTION

In the following description color references are made to The Royal Horticultural Society Color Chart (R.H.S.). The color values were determined indoors from plants grown outdoors in August 1994 in Hagenbach, Germany, or Hannover (Bundessortenamt).

Classification:

*Botanical.*—A hybrid of the species *Pelargonium zonale.*

*Commercial.*—Zonal geranium, cv. 'Lorca'.

Inflorescence:

*Umbel.*—Comprises approx. 38 flowers.

*Average diameter.*—Approx. 100 mm.

*Average depth.*—Approx. 55 mm.

*Peduncle length.*—Approx. 175–180 mm.

*Spring flowering response period.*—In Hannover (Bundessortenamt) early; 50% of plants with at least one flower opened 12 weeks after planting of unrooted cuttings.

*Outdoor flower production.*—The flower count in 1993 indicated between 65–70 flowers per plant for May 15 through Aug. 15 observation period.

*Durability.*—Medium rain and heat resistance.

Corolla:

*Blooming habit.*—Continuous, until frost destroys plant.

*Average diameter.*—Approx. 42 mm.

*Form.*—Semi-double; cup shaped when bloom first opens, flattening to shallow cup shape with maturity.

*Petals.*—Normally 8–9, upper petals approx. 2.2 cm across.

*Color (general tonality from a distance of three meters).*—pink/red purple.

*Color of upper and lower petals (top surface).*—R.H.S. 66C, macule type of marking R.H.S. 66 A; white zone with purple strips at base of upper petals and without striping on lower petals.

*Color of upper and lower petals (bottom surface).*—R.H.S. 69A.

*Petaloids.*—None.

*Pedicel length.*—Approx. 30–32 mm.

*Pedicel color.*—Light red (anthocyanin colored).

Bud: Size: Approx. 1.5–2.0 cm across. Shape: Initially ovate. Color: Green with few anthocyanin at the base. Sepals: Five, with pointed linear lanceolate; at time of petal appearance, about 10 mm in length.

Reproductive organs:

*Stamens.*— Anthers: 5 to 6. Filaments: Approx. 5–7 mm in length. Pollen: Red/orange in color.

*Pistils.*— No.: One. Length: Approx. 9 mm. Stigma: 7–8 lobes. Style: Approx. 3 mm in length; color: red.

*Ovaries.*—Green.

*Fruit.*—Partially fertile.

Plant:

*Foliage.*—Abundant quantity, leaves have zonation. Size: Approx. 9–10 cm across. Shape: Reniform. Margin: Bicrenate. Texture: Smooth. Color (upper surface): Medium green; R.H.S. 137 B/C. Color (zonation): Green (weak). Color (bottom surface): R.H.S. 137 C. Petioles: Approx. 9–10 cmm in length, green. Ribs & veins: Distinct venation on bottom side; not prominent on top surface.

*General appearance and form.*—Bushy. Internode length: Approx. 16 mm. Branching pattern: Self-branching from base; very good branching characteristics; 17 branches observed Aug. 15, 1994. Height: Approx. 20–22 cm from media surface.

CHART A

| | New Cultivar Name: 'Lorca' | Comparison Cultivar Name: 'Ganymed' |
|---|---|---|
| Branching pattern | 17 branches | 21 branches 15 Aug. 1994 |
| Umbel diameter | 100 mm | 88 mm |
| Average depth | 55 mm | 46 mm |
| Penduncle length | 175–180 mm | 140 145 mm |
| Pedicel length | 30–32 mm | 28–30 mm |
| Corolla diameter | 40–42 mm | 46–48 mm |

What is claimed is:

1. A new and distinct cultivar of geranium plant known as 'Lorca', as described and illustrated and particularly characterized by a pink with red/purple flower color, a semi-double flower form, medium green foliage, medium height, large umbels and early flower response.

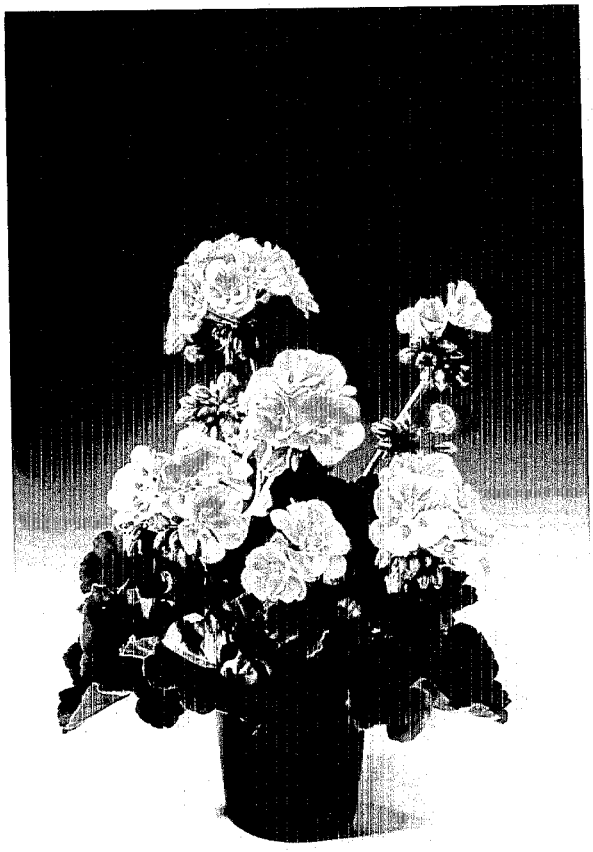

* * * * *